United States Patent

Varadaraj et al.

Patent Number: 5,493,050
Date of Patent: Feb. 20, 1996

[54] DIPHENYL DIALKYL METHANE SURFACTANTS

[75] Inventors: Ramesh Varadaraj, Flemington; Stephen Zushma, Clinton, both of N.J.

[73] Assignee: Exxon Research and Engineering Company, Florham Park, N.J.

[21] Appl. No.: 403,327

[22] Filed: Mar. 14, 1995

[51] Int. Cl.⁶ .......................... C07C 309/07; C07C 43/06; C07C 309/24
[52] U.S. Cl. .................. 562/41; 562/42; 568/640
[58] Field of Search .................. 562/41, 42; 568/640

[56] References Cited

FOREIGN PATENT DOCUMENTS 58084849  5/1983  Japan.

*Primary Examiner*—José G. Dees
*Assistant Examiner*—Joseph M. Conrad, III
*Attorney, Agent, or Firm*—Joseph J. Dvorak

[57] ABSTRACT

In one embodiment, the present invention relates to novel two tail—two head and two tail—one head surfactants. In one embodiment, the present invention comprises a novel composition of matter having the general formula:

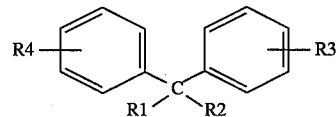

wherein R1 and R2 may be the same or different and are selected from linear or branched hydrocarbon chains with from 6 to 22 carbon atoms;
R3 is H, $SO^{13}{}_yM^+$, or $-O(CH2CH2O)_nX$;
R4 is $SO^-{}_yM^+$, or $-O(CH2CH2O)_nX$;
M is H, Li, Na, K, Rb or Cs;
n is an integer from 2 to 50;
y is 3 or 4; and,
X is H or $SO^{13}{}_yM^+$.
Preferably, in the above composition when R3 is other than H, R3=R4.

9 Claims, No Drawings

DIPHENYL DIALKYL METHANE SURFACTANTS

FIELD OF INVENTION

The present invention relates to novel surfactants with two hydrocarbon chains and one or two hydrophilic groups.

BACKGROUND OF THE INVENTION

Surfactants are amphiphilic molecules that manifest their properties at interfaces, e.g., the air-liquid, liquid-liquid and solid-liquid interfaces. They can be either water or oil soluble and are of considerable commercial importance because of their applications in petrochemical, pharmaceutical and soap industries. Generally, a surfactant molecule is characterized by the presence of a hydrophobic group, e.g., a long chain hydrocarbon (tail) attached to a hydrophilic group (head). The hydrophilic head group can be an anionic, cationic or non ionic moiety and accordingly, surfactants are classified as anionic, cationic or nonionic. The vast majority of synthetic surfactants known in the art are molecules with one long hydrocarbon chain attached to one head group. Variations reported in the art include branched hydrocarbon chains and fluorocarbon chains as tails. Surfactant molecules with two hydrocarbon chains attached to one or two head groups are relatively rare.

SUMMARY OF THE INVENTION

Broadly stated, the present invention relates to novel two tail—two head and two tail—one head surfactants. In one embodiment, the present invention comprises a novel composition of matter having the general formula:

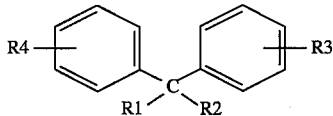

wherein R1 and R2 may be the same or different and are selected from linear or branched hydrocarbon chains with from 6 to 22 carbon atoms;
R3 is H, $SO^{13}_y M^+$, or $—O(CH2CH2O)_n X$;
R4 is $SO^-_y M^+$, or $—O(CH2CH2O)_n X$;
M is H, Li, Na, K, Rb or Cs;
n is an integer from 2 to 50;
y is 3 or 4; and,
X is H or $SO^-_y M^+$.
Preferably, in the above composition when R3 is other than H, R3=R4.

DETAILED DESCRIPTION OF THE INVENTION

The novel compounds of the present invention are prepared by the general procedure outlined below.

Alkylation Step

In the first step, an alkyl lithium compound, R1Li, wherein R1 is selected from linear or branched hydrocarbon chains with from 6 to 22 carbon atoms, is treated with a diarylalkene from the group consisting of: 1,1-diphenylethylene; 1,1 bishydroxyphenyl ethylene; 1-phenyl 1-hydroxyphenyl ethylene to provide a lithium containing intermediate. Typically, the contacting will be conducted in an inert solvent. Preferred solvents include ethers such as diethyl ether and tetrahydrofuran. Generally a molar excess of the alkyl lithium compound will be used.

For convenience, the alkyl lithium compound, R1Li, can be prepared in an ether solvent by contacting excess Li and an alkyl bromide at temperatures in the range of about −30° C. to about 20° C. Optionally, but preferably, an equimolar amount of tetramethyl ethylene diamine in an ether solvent is then added to the R1Li at a temperature of about −40° C. to about −50° C. The diarylalkene compound dissolved or slurried in an ether solvent is then slowly added to the reaction mixture at about −40° C. to about −50° C. After addition of the diarylalkene is complete, the reaction mixture is allowed to slowly rise to ambient temperature and stirred at this temperature for 18 to 20 hours. The lithium containing intermediate is subsequently contacted with R2Br wherein R2 is selected from linear or branched hydrocarbon chains with from 6 to 22 carbon atoms to provide the corresponding dialkylated derivative. The second alkylation step is carried out by adding R2Br in an ether solvent to the lithium containing intermediate at ambient room temperature and stirring for 2 to 3 hours.

When the alkylsubstituents R1 and R2 are different or when one of the phenyl rings of the diarylalkene is substituted, optical isomeric products result. When isomer separation is desired, fractional crystallization or HPLC techniques can be employed to isolate the optical isomers. Optionally, the mixture of isomers can be subjected to further functionalization without separation.

Functionalization Steps

(a) Sulfonation

The dialkyl derivative of the diaryl methane can be subjected to sulfonation by standard techniques known in the art. For example, the dialkylated derivative may be contacted with chlorosulfonic acid at the appropriate molar equivalent in an inert solvent such as methylene chloride at about 0° C. The sulfonic acid derivative is subsequently neutralized with the desired base to produce the sulfonate surfactant of the invention.

(b) Sulfation

The dialkyl derivative of the mono or dihydroxy substituted diaryl methane can be subjected to sulfation. For example, the dialkylated hydroxy derivative is dissolved in pyridine, cooled to 0° C., and then reacted with sufficient chlorosulfonic acid. Then the desired base, e.g., sodium hydroxide, potassium hydroxide or the like, is added to form the salt of the sulfate.

(c) Ethoxylaytion

Both of the dialkylated hydroxy and dihydroxy derivatives can be ethoxylated with ethylene oxide and conventional ethoxylation catalysts like sodium or potassium hydroxide. Typically, the ethoxylation reaction is carded out between about 0° C. to about 5° C. in solvents like tetrahydrofuran and dioxane.

To produce the ethoxysulfate, the ethoxylated product is sulfated by following the sulfation procedure described earlier.

Product isolation and purification is generally accomplished by vacuum distillation followed by fractional crystallization from suitable solvents such as acetone and acetone-methanol mixtures and the like.

EXAMPLE 1

This example details the synthesis of a two tail—two head surfactant of the invention wherein $R1=R2=n-C_{13}H_{27}$, $R3=R4=SO^-_yM^+$, M=Na and y=3.

Preparation of dialkylated derivative of 1,1 diphenylethylene (alkyl group=tridecane)

1-bromododecane, 62.3 gm (0.25 mole) in 100 mL of diethyl ether was rapidly added to a suspension of lithium, 3.5 gm (0.5 gm-atom), in 150 mL of diethyl ether cooled to −20° C. After addition, the mixture was stirred for 18 hrs. while the temperature rose to 25° C. The mixture was then cooled to −50° C. and tetramethyl ethylene diamine, 29.1 gm (0.25 mole), in 100 mL of diethyl ether was added, followed by 1,1-diphenylethylene, 22.6 gm (0.125 mole), diluted in 100 mL of diethyl ether. The mixture was stirred for 18 hours at room temperature. 1-bromotridecane, 34.2 gm (0.13 mole), in 100 ml of diethyl ether was added next and the mixture poured into water. The ether layer was washed successively with 10% hydrochloric acid, 10% sodium bicarbonate, saturated sodium chloride and dried over anhydrous magnesium sulfate. Ether was removed under vacuum to give crude product. The residue was distilled under reduced pressure (0.15 mm) to yield 44 gms of the dialkylated derivative (bp=235° C./0.15 mm Hg). $C^{13}$NMR (DMSO): §149.23, 127.96, 127.69, 125.37, 49.31, 37.61, 31.99, 30.41, 29.72, 29.47, 28.89, 22.74, 14.17. Elemental analysis: found % C 87.37, % H 13.10 Calculated: % C 87.9, % H 12.1.

Sulfonation of ditridecyl diphenyl methane

The ditridecyl diphenyl methane was sulfonated to obtain the pure sulfonated product according to the following procedure.

Chlorosulfonic acid, 9.8 gms (0.084 mole), in 100 mL methylene chloride was added dropwise into a solution of 15.6 gms (0.04 mole) of the dialkylated derivative, in 200 mL of methylene chloride at 0° C. and the mixture warmed to 25° C. and stirred. After 18 hours of reaction, methylene chloride was evaporated off and the solution neutralized with sodium methoxide to pH8 in methanolic medium. Methanol was then evaporated and a 2-propanol/water solution (50/50 volume ratio) added to the product and cooled to −10° C. to crystallize the sulfonated product.

The disulfonate product was further purified by High Performance Liquid Chromatography using a Varian Instrument LC 5000, with UV-50 detection. With the following conditions; Whatman Partisil 50DS-3 column, 80:20 acetonitrile/Waters PICA reagent at a flow rate of 1 mL/min., the retention time for the disulfonate product was 7.67 minutes.

Chemical Structure Characterization $C^{13}$ NMR (DMSO): §149.27, 144.76, 126.64, 125.26, 48.47, 43.01, 42.04, 4079, 39.88, 38.84, 37.80, 36.73, 36.55, 36.33, 31.34, 29.61, 29.05, 23.35, 22.11 18.81 $H^1$NMR: §7.33 (dd, 4H) 1.25–0.90 (m, 54H)

Elemental analysis :found % C 57.04, % H 8.37, % S 7.37, % Na 6.08 calcd % 63.54, % H 8.48, % S 8.71, % Na 6.21

Infrared (KBr pellet): 1335 cm$^{-1}$ and 1150 cm$^{-1}$ (antisymmetic and symmetric S=$O_2$ stretching).

EXAMPLE 2

This example details the synthesis and properties of a two tail - one head surfactant of the invention wherein $R1=R2=n-C_{13}H_{27}$, R3=H and R4=SOy-M+, M=Na and y=3. The surfactant was synthesized using the procedure described for Example 1 with the following change: sulfonation of the ditridecyl diphenyl methane was carded out with chlorosulfonic acid at a 1:1 mole ration. The product was isolated and purified by High Performance Liquid Chromatography using the conditions described for Example-1. The retention time was 19.3 minutes. Elemental analysis; found: % C 66.40, % H 8.67, % S 6.31, % Na 5.49 calculated: % C 73.76, % H 10.00, % S 5.06, % Na 3.62 $C^{13}$ NMP, (DMSO): §149.62, 144.85, 127.66, 127.15, 126.95, 125.56, 48.45, 43.84, 42.89, 41.88, 40.75, 39.88, 38.80, 37.76, 36.76, 31.66, 29.41, 22.41, 13.94.

The surfactants of Examples 1 and 2 are oil soluble. A 1% solution in dodecane was easily prepared and solubility was confirmed by UV absorption spectroscopy. Additionally a water-in-oil emulsion with 1 wt. % surfactant, 89 wt. % dodecane and 10 wt.% water was prepared.

What is claimed is:

1. A composition of matter having the general formula:

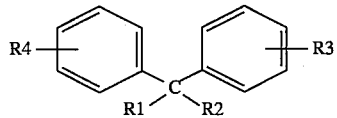

wherein R 1 and R2 may be the same or different linear or branched hydrocarbon chains with from 6 to 22 carbon atoms;
R3 is H, y , or $SO^-_yM^+$, or $-O(CH2CH2O)_nX$;
R4 is $SO^-_yM^+$, or $-O(CH2CH2O)_nX$;
M is H, Li, Na, K, Rb or Cs;
n is an integer from 2 to 50;
y is 3 or 4; and,
X is H or y $SO^-_yM^+$.

2. The composition of claim 1 wherein R3=R4 when R3 is other than H.
3. The composition of claim 2 wherein M is Na or K.
4. The composition of claim 2 wherein R3 and R4 are at para positions.
5. The composition of claim 1 wherein R1 and R2 are the same.
6. The composition of claim 5 wherein R3 is other than H and R4=R3.
7. The composition of claim 6 wherein R3 and R4 are at para positions.
8. The composition of claim 7 wherein R3 is $SO_yM^+$.
9. The composition of claim 7 wherein R3 is $-O(CH_2CH_2)_nX$.